US006331568B1

(12) United States Patent
Horrobin

(10) Patent No.: US 6,331,568 B1
(45) Date of Patent: Dec. 18, 2001

(54) PHARMACEUTICAL PREPARATION COMPRISING EICOSAPENTAENOIC ACID AND/OR STEARIDONIC ACID

(75) Inventor: David Frederick Horrobin, Stirling (GB)

(73) Assignee: Scotia Holdings PLC., Peasmarsh (GB)

(*) Notice: Subject to any disclaimer, the term of this patent is extended or adjusted under 35 U.S.C. 154(b) by 0 days.

(21) Appl. No.: 09/284,231

(22) PCT Filed: Oct. 7, 1997

(86) PCT No.: PCT/GB97/02738

§ 371 Date: Jun. 10, 1999

§ 102(e) Date: Jun. 10, 1999

(87) PCT Pub. No.: WO98/16216

PCT Pub. Date: Apr. 23, 1998

(30) Foreign Application Priority Data

Oct. 11, 1996 (GB) .................................................. 9621294
Dec. 16, 1996 (GB) .................................................. 9626062

(51) Int. Cl.$^7$ ........................ A61K 31/20; A61K 31/225
(52) U.S. Cl. ........................................... 514/560; 514/458
(58) Field of Search ...................... 514/560, 458

(56) References Cited

U.S. PATENT DOCUMENTS

| 5,837,731 | * 11/1998 | Vaddadi ................................ 514/560 |
| 5,840,944 | 11/1998 | Furihata et al. ...................... 554/175 |

FOREIGN PATENT DOCUMENTS

| 0347056 | 12/1989 | (EP) . |
| 0454102 | 10/1991 | (EP) . |
| 0599576 | 6/1994 | (EP) . |
| 2148713 | 6/1985 | (GB) . |
| 2229363 | 9/1990 | (GB) . |

OTHER PUBLICATIONS

Human Psychopharmacology, vol. 11, "Omega–3 Fatty Acid Supplementation in Schizophrenic Patients", pp. 39–46, 1996, Mellor.

* cited by examiner

Primary Examiner—Theodore J. Criares
(74) Attorney, Agent, or Firm—Jacobson Holman, PLLC

(57) ABSTRACT

A pharmaceutical preparation for the treatment of schizophrenia and/or tardive dyskinesia using an oil comprising eicosapentaenoic acid (EPA) and/or stearidonic acid (SA) in amounts of more than 20%, preferably more than 40% and very preferably more than 70% by weight of the total (preferably of the total unsaturated) fatty acids present.

10 Claims, No Drawings

PHARMACEUTICAL PREPARATION COMPRISING EICOSAPENTAENOIC ACID AND/OR STEARIDONIC ACID

FIELD OF THE INVENTION

The invention relates to fatty acid treatment in schizophrenia.

BACKGROUND

The essential fatty acids and their conversions in the body are shown in the following table.

| n-6 EFAs | | n-3 EFAs |
|---|---|---|
| 18:2n-6 | | 18:3n-3 |
| Linoleic acid (LA) | | α-Linolenic acid (ALA) |
| ↓ | δ-6-desacurase | ↓ |
| 18:3n-6 | | 18:4n-3 |
| γ-Linolenic acid (GLA) | | Stearidonic acid (SA) |
| ↓ | elongation | ↓ |
| 20:3n-6 | | 20:4n-3 |
| Dihomo-γ-linolenic acid (DGLA) | | Eicosatetraenoic acid |
| ↓ | δ-5-desacurase | ↓ |
| 20:4n-6 | | 20:5n-3 |
| Arachidonic acid (AA) | | Eicosapentaenoic acid (EPA) |
| ↓ | elongation | ↓ |
| 22:4n-6 | | 22:5n-3 |
| Adrenic acid (AdrA) | | |
| ↓ | δ-4-desacurase | ↓ |
| 22:5n-6 | | 22:6n-3 |
| | | Docosahexaenoic acid (DHA) |

The acids, which in nature are of the all-cis configuration, are systematically named as derivatives of the corresponding octadecanoic, eicosanoic or docosanoic acids, e.g.LA z,z-octadeca-9,12-dienoic acid or DHA z,z,z,z,z,z-docosa-4,7,10,13,16,19-hexaenoic acid, but numerical designations based on the number of carbon atoms, the number of centres of unsaturazion and the number of carbon atoms from the end of the chain to where the unsaturation begins, such as, correspondingly, 18:2 n-6 or 22:6 n-3, are convenient. Initials, e.g. EPA, and shortened forms of the name e.g. eicosaerntaenoic acid, are used as trivial names in some instances.

In previous patent applications EPA-0347056 and EPA-0599576 we have drawn attention to the action of various essential fatty acids in schizophrenia and have claimed the use of these fatty acids in treatment. We have particularly drawn attention to the low red cell levels of arachidonic acid (AA) and docosahexaenoic acid (DHA) and to the use of these fatty acids.

Present Work

We have now unexpectedly found that one Particular essential fatty acid which was previously accorded only a minor role is in fact particularly effective in treatment. This is eicosapentaenoic acid (EPA; 20:5n-3) which is present in the brain in only small amounts compared to AA and DHA. However, in a trial of treatment we have found that EPA is exceptionally effective in treatment of schizophrenia. Particularly effective are preparations comprising EPA in amounts of more than 20% of the total fatty acids present (preferably the total unsaturated fatty acids present), preferably more than 40% and very preferably more than 70%.

Studies of the use of omega-3 essential fatty acids in treatment, using a mixture of DHA and EPA, have previously shown modestly beneficial effects (Mellor et at, Human Psychopharmacology 11:39–46, 1996). The preparation used contained 18% of EPA and 12% of DHA and so far as this disclosure goes the therapeutic effects could have been caused by either component or both. An analysis of the relationship between fatty acid change and schizophrenia symptoms showed that a rise in the total omega-3 content of red cell membranes was associated with a fall in schizophrenic symptoms.

We therefore decided to try to determine the relative importance of EPA and DHA in schizophrenia. A study was carried out with 30 schizophrenia patients, most of whom had both positive and negative symptoms as shown by the positive and negative symptom scale (PANSS) and also had some evidence of tardive dyskinesia as shown by the abnormal involuntary movements scale (AIMS). Patients were randomly assigned on a double blind basis to treatment with 20 ml of a placebo emulsion, 20 ml of a 40% emulsion providing 8 g of oil containing approximately 2.0 g of EPA and 0.4 g of DHA per day ('EPA group'), and 20 ml of an emulsion providing approximately 2.3 g of DHA and 0.5 g of EPA per day ('DHA group') in 8 g of oil. Patients were scored at baseline and at the end of 12 weeks of treatment. In the placebo group, 9 patients were unchanged or deteriorated on the PANSS and AIMS scores and one improved. In the DHA group, seven patients were unchanged or deteriorated and three patients improved. In contrast, in the EPA group one patient was unchanged but nine patients showed improvement. The improvement was seen in both the negative and positive symptom scores and in the AIMS score. There was therefore a broad spectrum improvement in all aspects of the schizophrenia syndrome. The DHA group was not significantly different from placebo whereas the EPA group was significantly better than both the DHA group and the placebo group ($p<0.02$ in both cases).

It is therefore possible to conclude that the main therapeutic effect of treatment with EFAs is attributable to the effect of EPA. The other EFAs may contribute to some degree but there can be no doubt that EPA is primarily responsible for the positive effects of treatment with omega-3 EFA preparations. We concluded that EPA should also be effective in other psychiatric disorders such as Alzheimer's disease and depression since low levels of n-3 fatty acids have been shown in the blood and/or the brain of patients with these disorders also Two patients with severe depression not responsive to the usual anti-depressants were therefore treated with the EPA formulation as used in the schizophrenia trial. Within 4 weeks both had shown remarkable improvement in their symptoms.

While we cannot be certain of the mechanism by which EPA is working, one possibility is that it is inhibiting the enzyme, phospholipase A2. There is considerable evidence that phospholipase (PL) A2 activity is elevated in schizophrenia (Horrobin et al, Schizophrenia Research 1994; 13: 195–207). Compounds which safely inhibit PLA2 might therefore be expected to have a therapeutic effect. In in vitro studies of the effects of fatty acids on PLA2 activity we have found that EPA is a potent inhibitor, whereas the relatively similar fatty acid, DHA is not. This might explain why DHA did not prove effective in the clinical studies.

We have further found that another n-3 fatty acid, stearidonic acid (18:4 n-3), is as effective in inhibiting, PLA2 as is EPA. EPA and SA are 20- and 18-carbon fatty acids which have in fact been shown to inhibit the activity of phospholipase $A_2$ (Finnen, Biochem Soc. Trans 1991; 19:915). In contrast, DHA is A 22-carbon fatty acid which like other 22-carbon acids does not inhibit phospholipase. This may offer an explanation for the differences between EPA and DHA since there is evidence for overactivity of phospholipase A$_2$ in schizophrenia. We therefore propose that stearidonic acid will be effective in treating schizophrenia and the other disorders and we include its use for that purpose alone or with EPA.

The n-6 EFAs such as linoleic acid, gamnmalinolenic acid (GLA) dihomogammalinolenic acid (DGLA) and arachidonic acid (AA) are important in brain structure. GLA can be metabolised to DGLA and AA. We therefore tried to see whether the addition of an oil containing linoleic acid and GLA would be beneficial in two individuals who had responded to EPA. In fact their condition appeared to be less good with addition of the n-6 EFAs. It is therefore better to treat with EPA preparations in which the levels of n-6 EFAs are kept at a low level compared to the concentration of EPA. Either n-6 EFAs should be absent or if present at a ratio to EPA of not more than 1:3, preferably 1:4 or less.

In any case to ensure that the effects secured are not countered the weight ratio of SA/EPA to any DHA present is desirably not less than 3:1 by weight and desirably 4:1 or more.

STATEMENT OF INVENTION

The invention is set out in the claims herein but inter alia provides a pharmaceutical preparation for the treatment of schizophrenia and/or tardive dyskinesia using an oil comprising eicosapentaenoic acid (EPA) and/or stearidonic acid (SA) in amounts of more than 20%, preferably more than 40% and very preferably more than 70% by weight of the total (preferably of the total unsaturated) fatty acids present and wherein the weight ratio of SA/EPA to n-6 EFAs present is not less than 3:1 and is preferably 4:1 or more, or n-6 EFAs are absent. Corresponding methods of treatment, and methods of preparation of medicaments, wherein such oils as used, are also within the invention, as are corresponding treatments of depression or Alzheimer's disease or other dementias.

The EPA can be provided in any appropriate way which will elevate the levels of EPA in the blood. Mono-, di-, and tri-glycerides, mono- or di-esters, salts, cholesterol esters, amides, phospholipids, free acids or any other appropriate form may be used to deliver the EPA. Mono or diesters of EPA as specified in previous applications where the present inventor is a co-inventor (PCT/GB96101052 and 01053), published respectively as WO96/34855 and WO96/34846 are particularly convenient forms in which the EPA may be administered. The EPA may be derived from fish or marine mammal oils, microbial oils or even from total chemical synthesis. The EPA dose used may range from 10 mg to 100 g/day, preferably 100 mg to 20 g/day and very preferably from 500 mg to 10 g/day. Oral, enteral, parenteral, topical, or any other appropriate route of administration may be used. Steardonic acid may be provided in similar doses and in similar ways, alone or with the EPA

EXAMPLES

The study described above illustrates treatment according to the invention but examples of suitable formulations are as follows:

1. Soft gelatine capsules, each containing 200 mg of EPA in the form of one of the following:

a) An oil containing 22% EPA derived from marine or microbial sources.

b) An oil containing 56% EPA derived from marine or microbial sources.

c) An oil containing 75% of EPA derived from marine or microbial sources.

d) An oil containing 95% of EPA derived from marine, microbial or synthetic sources.

e) EPA 1–3 propane diol diester.

2. Oils as in examples la to le but formulated as an emulsion for oral administration. The emulsion may contain 5 to 50% of the oil emulsified with emulsifying agents known to these skilled in the art including natural, synthetic and semi-synthetic agents such as phospholipids and galactolipids, the latter for example as described in PCT SE95/00115 published as WO95/20943.

3. Emulsions as in 2 but sterilised and appropriately formulated for intravenous administration.

4. Oils as in examples la to le, sterilised ad formulated for intramuscular or sub-cutaneous injection.

5. Oils as in examples la to le formulated for topical administration using patch or other technologies known to those skilled in the art.

6–10. As Examples 1–5 except that stearidonic acid is used instead of EPA or in admixture with it e.g. half and half.

What is claimed is:

1. A method of treatment of schizophrenia, whereby an oil is administered comprising i) an essential fatty acid (EFA) selected from the group consisting of eicosapentaenoic acid (EPA) and stearidonic acid (SA) in amounts of more than 20% by weight of the total fatty acids present and ii) optionally, n-6 EFAs, wherein the weight ratio of SA/EPA to said n-6 EFAs, if present, is not less than 3:1.

2. A method of treatment according to claim 1 wherein said EFA comprises more than 40% of the total fatty acids present.

3. A method of treatment according to claim 1 wherein said EFA comprises more than 70% of the total fatty acids present.

4. A method of treatment according to claim 1 wherein the weight ratio of said EFA to said n-6 EFAs present is 4:1 or more.

5. A method of treatment according to claim 1 wherein said n-6 EFAs are absent.

6. A method of treatment according to claim 1 wherein the weight ratio of said EFA to any DHA, if present, is not less than 3:1.

7. A method of treatment according to claim 1 wherein the weight ratio of said EFA to any DHA, if present, is 4:1 or more.

8. A method of treatment according to claim 1 wherein doses of 10 mg to 100 g of said EFA are administered daily.

9. A method of treatment according to claim 1 wherein doses of 100 mg to 20 g of said EFA are administered daily.

10. A method of treatment according to claim 1 wherein doses of 500 mg to 10 g of said EFA are administered daily.

* * * * *